US012186359B2

(12) United States Patent
Allegretti et al.

(10) Patent No.: US 12,186,359 B2
(45) Date of Patent: Jan. 7, 2025

(54) COMPOSITION CONTAINING BRANCHED-CHAIN AMINO ACIDS

(71) Applicant: DOMPÉ FARMACEUTICI S.P.A., Milan (IT)

(72) Inventors: Marcello Allegretti, Rome (IT); Andrea Aramini, L'Aquila (IT); Gianluca Bianchini, L'Aquila (IT)

(73) Assignee: DOMPÉ FARMACEUTICI S.P.A., Milan (IT)

( * ) Notice: Subject to any disclaimer, the term of this patent is extended or adjusted under 35 U.S.C. 154(b) by 643 days.

(21) Appl. No.: 17/619,739

(22) PCT Filed: Jun. 29, 2020

(86) PCT No.: PCT/EP2020/068224
§ 371 (c)(1),
(2) Date: Dec. 16, 2021

(87) PCT Pub. No.: WO2020/260689
PCT Pub. Date: Dec. 30, 2020

(65) Prior Publication Data
US 2022/0296670 A1    Sep. 22, 2022

(30) Foreign Application Priority Data
Jun. 28, 2019  (IT) .................... 102019000010401

(51) Int. Cl.
| | | |
|---|---|---|
| *A61K 38/05* | (2006.01) | |
| *A23L 33/175* | (2016.01) | |
| *A23L 33/18* | (2016.01) | |
| *A61K 31/198* | (2006.01) | |
| *A61K 31/223* | (2006.01) | |
| *A61P 21/00* | (2006.01) | |

(52) U.S. Cl.
CPC ............ *A61K 38/05* (2013.01); *A23L 33/175* (2016.08); *A23L 33/18* (2016.08); *A61K 31/198* (2013.01); *A61K 31/223* (2013.01); *A61P 21/00* (2018.01)

(58) Field of Classification Search
CPC .... A61K 38/05; A61K 31/198; A61K 31/223; A61P 21/00; A23L 33/18; A23L 33/175
USPC .......................................................... 514/564
See application file for complete search history.

(56) References Cited

FOREIGN PATENT DOCUMENTS

| | | |
|---|---|---|
| JP | 2000026289 | 1/2000 |
| JP | 2000026298 | 1/2000 |
| RU | 2578463 | 3/2016 |
| WO | WO 2006105112 | 10/2006 |
| WO | WO2011011252 | 1/2011 |
| WO | WO2017014120 | 1/2017 |

OTHER PUBLICATIONS

Database WPI, Week 200016. Thomson Scientific, London, GB; AN 2000-176884, XP-002797405, Jan. 25, 2000.
Database WPI, Week 200016, Thomson Scientific, London, GB; AN 2000-176885, XP-002797406, Jan. 25, 2000.
Database WPI, Week 201713, Thomson Scientific, London, GB: AN 2017-08042D, XP-002797407, Jan. 25, 2000.
Eley, et al., Biochem J., 2007, 407, 113-120.
English Abstract for RU 2578463, Mar. 27, 2016.
Maki, et al., Nutrition Research, 2012, 32, 676-683.
Newsholme, et al., J Nutr., 2006, 136, 274S-6S.
Okimura, In: Rajendram, R., Preedy, V., Patel, V. (eds) Branched Chain Amino Acids in Clinical Nutrition. Nutrition and Health. 2015, pp. 49-63.
Pierno, et al., J Physiol. 2007, 584, 983-995.
Sharp, et al., Journal of Strength Conditioning and Research, 2010, 24, 1125-1130.
International Search Report for PCT/EP2020/068224 dated Aug. 27, 2020.

*Primary Examiner* — Kristin A Vajda
(74) *Attorney, Agent, or Firm* — HUESCHEN AND SAGE

(57) ABSTRACT

The present invention relates to compositions comprising branched-chain amino acids (BCAA) and the dipeptide L-Alanyl-L-alanine and their use for improving the performance and recovery during physical activity and for the prevention and/or treatment of muscle wasting associated to pathological or age-related conditions.

15 Claims, 7 Drawing Sheets

COMPOSITION CONTAINING BRANCHED-CHAIN AMINO ACIDS

FIELD OF THE INVENTION

The present invention relates to a combination of branched-chain amino acids (BCAA) and the dipeptide L-Alanyl-L-alanine, related pharmaceutical compositions and dietary supplements comprising the same and uses thereof for improving the performance and recovery during physical activity and for use as a medicament for the prevention and/or treatment of muscle wasting associated to pathological or age-related conditions.

BACKGROUND OF THE INVENTION

Skeletal muscle is a plastic organ that is maintained by multiple pathways regulating cell and protein turnover. Skeletal muscle proteins are constantly and simultaneously synthesized and degraded. The amount of protein in the muscle and the maintenance of skeletal muscle mass in the mature individual depends on the net muscle protein balance (NBAL), the difference between skeletal muscle protein synthesis (MPS) and breakdown (MPB). Growth factors, hormones, cytokines, nutrients, and mechanical loading can activate cellular signaling pathways that favor either protein synthesis or degradation leading to a gain or loss, respectively, of skeletal muscle mass.

Muscles are not only important for locomotion and the maintenance of posture but also provide the largest protein reservoir in the body and serve as a source of amino acids that can be used for energy production and gluconeogenesis by various organs (including the heart, liver and brain) during catabolic metabolism.

A number of conditions are associated to a negative net muscle protein balance. During some pathological conditions, an increased activation of proteolytic systems can be present, thereby contractile proteins and organelles are removed from the muscle, resulting in muscle atrophy. Muscle wasting occurs systemically in older people (a condition known as age-related sarcopenia), as a physiological response to fasting, malnutrition or immobility (e.g. postoperative) and in pathological conditions such as neuromuscular degenerative disorders (e.g. muscular dystrophy or atrophy), chronic obstructive pulmonary disorder, cancer-associated cachexia, diabetes, renal failure, cardiac failure. Cushing syndrome, sepsis, burn injuries, uremia, cirrhosis and AIDS.

Excessive loss of muscle mass is associated with poor prognosis in several diseases.

Muscle loss may also be observed as a consequence of a sustained high-intensity exercise, such as for example running a marathon which stimulate muscle catabolism in order to provide amino acids as a substrate for energy production.

Sports supplements are widely used by athletes to ensure an adequate carbohydrate and protein availability and thus avoid muscle catabolism.

Essential amino acids are biomolecules that cannot be synthesized by the human body and therefore need to be supplied in the diet. The branched-chain amino acids (BCAAs) Leucine, Valine, and Isoleucine account for 35% of the essential amino acids in muscles and are the most intensively-consumed essential amino acids during sporting activity.

It has also been demonstrated that the serum concentration of essential amino acids may affect the development and extent of fatigue reached during an endurance competition.

Furthermore, amino acids are theorized to enhance performance in a variety of ways, such as modifying fuel utilization during exercise and preventing mental fatigue and Newsholme E A et al, J Nutr. 2006, 136; 274S-6S; C. P. M. Sharp et al, Journal of Strength and Conditioning Research 2010, 24(4)/1125-1130).

A number of studies have demonstrated that BCAAs serve as substrate for protein synthesis and energy production and perform several metabolic and signaling functions, particularly via the activation of mTOR signaling pathway.

These effects are realized by the BCAAs themselves, especially Leucine, and by their metabolites. In fact, Leucine stimulates protein synthesis through the mTOR signaling pathway and phosphorylation of translation initiation factors and ribosomal proteins, while the inhibitory effect on proteolysis is mainly mediated by HMG (β-hydroxy-β-methyl-butyrate) and branched-chain keto acids.

Interestingly, unlike most amino acids, the initial step of BCAAs catabolism takes place in skeletal muscle and not in the liver, because of the higher activity in this tissue of branched-chain-amino-acid aminotransferase (BCAT), the first enzyme responsible for BCAAs catabolic pathway. This gives a unique advantage to BCAA-based nutritional formulas compared with others as regards the effect on the improvement of muscle and brain function, since circulating BCAAs rapidly increase after protein intake and become readily available to extrahepatic tissues.

In view of the above, supplementation of BCAAs is nowadays widely used for athletes, to both limit the development of central fatigue and support muscle health and anabolism.

L-Alanine is a gluconeogenic amino acid and is one of the products of BCAAs catabolism.

Friliver® Sport Performance (Dompé Farmaceutici S.p.A.) is a marketed dietary supplement comprising both BCCAs and L-Alanine and used to improve sport performance and to reduce fatigue.

There is still a need to develop improved, more effective compositions to be used as supplements in athletes. Furthermore, it is strongly felt the need to develop compositions that are effective in prevention and/or treatment of muscle wasting, for example associated to age, fasting, malnutrition, immobility or pathological conditions.

SUMMARY OF THE INVENTION

The present inventors have surprisingly found in animal models that oral administration of a combination containing BCAAs and the dipeptide L-Alanyl-L-alanine (Ala-Ala) is particularly effective in improving muscle function, structure and metabolism both in case of intense training and in those conditions wherein muscle wasting occurs.

Accordingly, it is an object of the present invention a composition comprising the branched-chain amino acids (BCCAs) and the peptide L-Alanyl-L-alanine.

It is a further object of the present invention the above composition for use as a medicament for the prevention and/or treatment of muscle wasting associated to pathological conditions, age-related condition, malnutrition, immobility or lasting.

Another object of the present invention is the use of the above composition as a dietary supplement for physical exercise to improve muscular performance and/or recovery, and/or to reduce muscular fatigue.

Another object of the present invention is a pharmaceutical composition or a dietary supplement comprising the above combination of branched-chain amino acids (BCCAs)

and L-Alanyl-L-alanine as the active principle, with at least one pharmaceutically or nutraceutical acceptable vehicle, excipient and/or adjuvant.

Definitions

As used herein, the term "branched-chain amino acids (BCAAs)" refers to the amino acids L-Isoleucine, L-Leucine, and L-Valine.

As used herein, the term "L-Alanyl-L-alanine" or "Ala-Ala" are indifferently used to indicate a dipeptide consisting of two L-alanine units joined by a amidic linkage. Instead, the term "Ala" refers to the amino acid L-alanine alone.

FIGURES

FIG. 1 shows the forelimb force normalized on body weight for mice undergoing a training protocol and treated with Vehicle, BCAA (BCAA), BCAA plus L-Alanine (BCAA+2Ala) or BCAA plus L-Alanyl-L-alanine (BCAA+Ala-Ala), as described in Example 1. (ANOVA at T3: * BCAA+Ala-Ala vs BCAA+2Ala ($p<0.005$), vs BCAA ($p<0.005$) and vs. vehicle ($p<0.005$); §§ BCAA+2ALA vs vehicle ($p<0.01$). ANOVA at T4:  BCAA+Ala-Ala vs BCAA+2Ala ($p<0.01$), vs BCAA ($p<0.01$) and vs vehicle ($p<0.005$); §§ BCAA+2ALA vs BCAA ($p<0.05$) and vs vehicle ($p<0.01$).

DETAILED DESCRIPTION OF THE INVENTION

Figure 1:
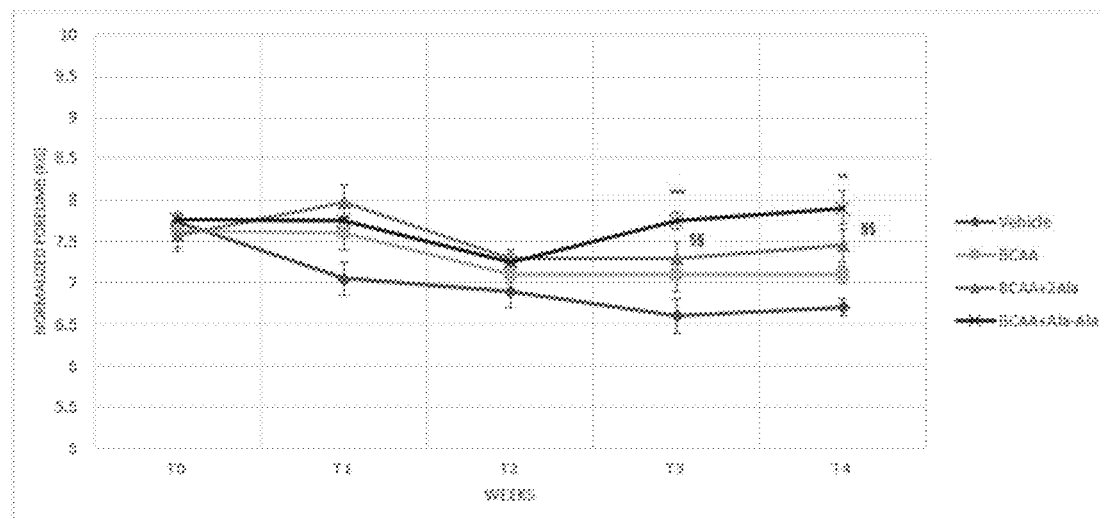

As will be demonstrated in the Experimental Section, the present inventors have unexpectedly found that a formulation comprising BCAAs in combination with the dipeptide L-Alanyl-L-alanine is particularly effective in improving muscle function, structure and metabolism. Surprisingly, this effect is observed both in case of intense training and in pathological conditions of muscle wasting. The data obtained also demonstrate that that the dipeptide L-Alanyl-L-alanine significantly increases the absorption of BCAAs when these are administered orally and induce their preferential distribution in the muscle.

Therefore, it is a first object of the present invention a composition comprising the branched-chain amino acids (BCCAs) L-Leucine, L-Valine and L-Isoleucine in combination with the peptide L-Alanyl-L-alanine.

Preferably, in the above composition, the weight ratio L-Leucine:L-Valine:L-Isoleucine is between 2:1:1 and 8:1:1.

According to a preferred embodiment of the invention, L-Leucine, L-Valine and L-Isoleucine are present in the composition in a weight ratio of 2:1:1, respectively.

According to another preferred embodiment of the invention, L-Leucine, L-Valine and L-Isoleucine are present in the composition in a weight ratio of 4:1:1.

According to another preferred embodiment of the invention, L-Leucine, L-Valine and L-Isoleucine are present in the composition in a weight ratio of 8:1:1.

Preferably, in the composition of the invention the weight ratio between BCAAs and the peptide L-Alanyl-L-alanine is between 5:1 and 1:1, preferably it is between 3:1 and 1.5:1, more preferably it is 2:1 or 1.6:1.

According to a particularly preferred embodiment, in the composition of the invention, the weight ratio L-Leucine:L-Valine:L-Isoleucine:L-Alanyl-L-alanine is between 2:1:1:1 to 2:1:1:3.6, more preferably it is 2:1:1:2.5 or 2:1:1:2.

Preferably, the composition of the invention does not contain further aminoacids or peptides in addition to the BCAAs and L-Alanyl-L-alanine.

Preferably, the composition of the invention is suitable for oral administration.

According to one embodiment, the composition according to the first object of the invention is a pharmaceutical composition.

Said pharmaceutical composition preferably comprises said BCAAs and the dipeptide L-Alanyl-L-alanine in admixture with at least one pharmaceutically acceptable vehicle, excipient or adjuvant. The composition may comprise any of the pharmaceutically acceptable vehicles, excipients or adjuvants known in the art. For example, the pharmaceutical composition according to the invention may contain customary ingredients such as fillers, binders, lubricants, flavoring agents, stabilizers, pH adjusters, disintegrating agents, preservatives.

Preferably, the pharmaceutical composition of the invention is suitable for oral administration.

The pharmaceutical composition for oral administration of the invention may be a solid or liquid formulation.

Preferred formulations of the invention contemplate pharmaceutical forms selected from the group consisting of granulate, tablet, capsule, effervescent tablet, oral suspension, emulsion, powder, solution, or syrup. The most preferred pharmaceutical form according to the invention is a granulate for oral suspension or dissolution in a liquid, preferably water.

According to an alternative embodiment, said composition is a dietary supplement.

Preferably, said dietary supplement comprises said BCAAs and the dipeptide L-Alanyl-L-alanine in admixture with at least one acceptable vehicle or excipient for human use.

Preferably, said dietary supplement is in form of a tablet, capsule or liquid, more preferably it is liquid.

According to one embodiment, said dietary supplement can be in the form of a drink or a food composition.

Preferably, the composition of the invention, preferably as pharmaceutical composition or dietary supplement, is formulated so as to contain the following amount of BCAAs and dipeptide per unit dose: between 0.6 and 1 g, preferably 0.8 g of L-Leucine, between 0.3 and 0.5 g, preferably 0.4 g of L-Isoleucine, between 0.3 and 0.5 g, preferably 0.4 g of L-Valine and from 0.5 g to 1.5 g, preferably from 0.8 g to 1.5 g, more preferably 0.8 g of L-Alanyl-L-alanine.

A second object of the invention is the above disclosed composition for use as a medicament.

As demonstrated in the Experimental Section, the composition according to the invention significantly improves the neuromuscular function of the plantar flexor muscle when administered in an animal model of muscle wasting.

Accordingly, in a preferred embodiment, the above composition is for use in the prevention, ameliorating and/or treatment of muscle wasting associated to:
  i. pathological conditions, preferably selected from the group consisting of neuromuscular degenerative disorders, such as muscular dystrophy or muscular atrophy; chronic obstructive pulmonary disorder; cancer-associated cachexia; diabetes; renal failure; cardiac failure; Cushing Syndrome; sepsis; burn injuries; uremia; cirrhosis; and AIDS;
  ii. age-related condition, preferably sarcopenia; or
  iii. malnutrition, immobility or fasting.

In all the above applications, the composition according to the invention is preferably administered twice per day.

As demonstrated in the Experimental Section, the composition of the invention is particularly useful to be administered before, during or after physical exercise to improve muscular performance and/or recovery, and/or to reduce muscular fatigue.

Accordingly, a third object of the invention is the use of the above composition, preferably as a dietary supplement, before, during and after physical exercise.

It is a further object of the invention the use of the above composition to improve muscular performance and/or recovery, and/or to reduce muscular fatigue before, during or after physical exercise.

In the above use, the composition is administered as a single dose of between 0.6 and 1 g, preferably 0.8 g of L-Leucine, between 0.3 and 0.5 g, preferably 0.4 g of L-Isoleucine, between 0.3 and 0.5 g, preferably 0.4 g of L-Valine and from 0.5 g to 1.5 g, preferably from 0.8 g to 1.5 g, more preferably 0.8 g of L-Alanyl-L-alanine, on an as-needed basis.

EXPERIMENTAL SECTION

All the experiments were conducted in conformity with the Italian Guidelines for Care and Use of Laboratory Animals (D.L.116/92), and with the European Directive (2010/63/UE). The study belongs to studies approved by national ethic committee for research animal welfare of the Italian Ministry of Health as far as ethical issues and adherence to law are concerned. Most of the experimental procedures used in the present study are approved by international scientific networks working on animal models of neuromuscular diseases (http://www.treat-nmd.eu/research/preclinical/SOPs/).

Statistics

All experimental data were expressed as mean±standard error of the mean (S.E.M.). Multiple statistical comparisons between groups were performed by one-way ANOVA, with Bonferroni's t test post hoc correction when the null hypothesis was rejected ($p<0.05$), to allow a better evaluation of intra- and inter-group variability and avoiding false positive. If necessary, single comparisons between two means (modified formulations vs vehicle or vs standard formulation).

Example 1—Efficacy of Formulation During Training a) Experimental Groups and Protocol 10-week-old, male C57BL/6J wild type (WT) mice purchased from Charles River (Calco, Italy) were used in the study. All mice were acclimatized for one week in the animal facility, prior to the start of the experimental protocol; then, they were d to each treatment group based on their body weight and on absolute and normalized forelimb grip strength values, in order to create homogeneous cohorts at the beginning of the study.

Experiments, data collection and analysis were carried out in blind by the experimenters.

The mice were divided in the following groups:
1. Control group (n=5):
Mice not subjected a physical exercise protocol and watered with vehicle;
2. Vehicle group (n=5):
Mice subjected to a physical exercise protocol described below and watered with vehicle (filtered tap water).
3. BCAA Group (n=8):
Mice subjected to a physical exercise protocol described below and watered with an aqueous solution containing a mixture of L-Leucine. L-Valine and L-Isoleucine in a weight ratio 2:1:1. Each mouse received a total amount of 328 mg/Kg of L-Leucine, 164 mg/Kg of L-Valine and 164 mg/Kg of L-Isoleucine.
4. BCAA and L-Ala Group (n=8):
Mice subjected to a physical exercise protocol described below and watered with an aqueous solution a mixture of L-Leucine, L-Valine, L-Isoleucine and L-Alanine in a weight ratio 2:1:1:2. Each mouse received a total amount of 328 mg/Kg of L-Leucine, 164 mg/Kg of L-Valine, 164 mg/Kg of L-Isoleucine and 328 mg/Kg of L-Alanine.
5. BCAA and L-ala-L-ala (n=8:
Mice subjected to a physical exercise protocol described below and watered with an aqueous solution containing a mixture of L-Leucine, L-Valine, L-Isoleucine and a L-Alanyl-L-alanine dipeptide in a in a weight ratio 2:1:1:2. Each mouse received a total amount of 328 mg/Kg of L-Leucine, 164 mg/Kg of L-Valine, 164 mg/Kg of L-Isoleucine and 328 mg/Kg of L-Alanyl-L-alanine.

The aqueous solutions used for groups 3 to 5 were prepared by dissolving the amino acids and the dipeptide in filtered tap water, in order to obtain the desired final concentration. This was obtained by direct preparation, considering the weekly amount of water consumed by each mouse and its body weight.

Mice groups 2 to 5 were subjected to the following physical exercise protocol.

In details, all mice were made to run on a motor horizontal treadmill (Columbus Instruments, USA), according to the following two phase schedule:

Phase 1: this consisted in 3 weeks of pre-treatment exercise sessions (45 min, 5 days/week), in order to make the mice adapt to the procedure, progressively reaching the target workload. All mice were made to run starting with a 5 min warm-up at 5 m/min, and then increasing the speed of 1 m/min each minute, until reaching the maximum velocity which was maintained until the end of the exercise bout. Maximum speed was incremented on a weekly basis, until reaching the target velocity of 25 m/min.

Phase 2: this phase consisted in 4 weeks of exercise sessions (45 min, 5 days/week) at maximum workload, starting with a warm-up of 15 min at 10 m/min, and then increasing the speed of 1 m/min each minute, reaching a maximum velocity of 25 m/min, which was maintained until the end of the exercise bout.

The treatment with water (group 2) or with the different solutions (groups 3-5) was carried out in parallel with phase 2.

For the whole duration of the study, all mice were maintained on a controlled diet with a daily amount of chow of 4-5 g/mouse.

b) Analysis of Mice Parameters
i. Methods

In vivo and ex vivo parameters were collected from the animals.

Collection of In Vivo Parameters

The following data were monitored during the exercise protocol:

1. Body Weight Variations and Water Intake.
2. Forelimb Grip Strength

At day 0 (T0), 7 (T1), 14 (T2), 21 (T3) and 28 (T4) of phase 2 of the exercise protocol, the forelimb strength was measured for each mouse by means of a grip strength meter (Columbus Instruments, USA). Maximal force (absolute and normalized to body weight) developed against gentle pull away from grip over 5 determination/animal was used for statistical analysis.

3. In Vivo Determination of Salivary IgA Levels by Enzyme-Linked Immunosorbent Assay (ELISA).

Saliva samples were collected from the oral cavity of each mouse by using a micropipette, ~5 minutes after intraperitoneal injection of pilocarpine to stimulate saliva secretion (1 mg/kg, Sigma-Aldrich, USA). Then, saliva was immediately placed in micro-centrifuge tubes containing PMSF (Sigma-Aldrich, USA) to inhibit proteases and kept on ice. Samples were clarified by centrifugation at 16,000×g for 10 min at 4° C.; the surnatant was stored at −80° C. until the analyses were performed. Salivary IgA levels were quantified using a Mouse IgA Ready-SET-Go! ELISA kit (eBioscience, Vienna, Austria), according to the manufacturer's protocol.

4. Determination of Plasma Levels of Lactate Dehydrogenase (LDH) by Spectrophotometry.

Blood was obtained from cardiac puncture of left ventricle with a heparinized insulin syringe and collected in heparinized tubes. The samples were processed within 30 minutes after collection. Platelet-poor plasma was obtained after two consequential centrifugation steps (20 mins, 4000 rpm, 4° C.; 10 min, 12000 rpm, 4° C.).

Lactate dehydrogenase (LDH) activity was determined by means of commercially available kits (CK NAC LR and LDH LR, SGM Italy). The instrument was set to a wavelength of 340 nm, at 37° C.

Collection of Ex Vivo Parameters

At the end of week 4 of phase 2 the animals were anesthetized intraperitoneally with a combination of ketamine (100 mg/kg) and xylazine (16 mg/kg) and sacrificed. Gastrocnemius and Tibialis muscles were dissected from each mouse and frozen until analysis.

These samples were stored at −80° C. in order to be used for planned end point assessments. The following analysis were carried out:

1. Determination of the Protein Content by Bradford Assay in Gastrocnemius Muscle.

The buffer used in the assay was constituted of the following ingredients dissolved in 100 mL of water: 1 mL Triton X-100, 2 ml Tris HCL pH8, 2.74 mL NaCl (5 M) 10 mL glycerol, 1 mL EDTA 0.5 M pH 8. PMSF (protease inhibitor) 100 mM in EtOH is added before the use. Gastrocnemio muscles were homogenized in buffer with a dilution 1/5 w/v (g/mL) using the CK14 tube (Precellys Lysing kit) with Bertin homogenizer.

Samples were then centrifuged after homogenization and lysates were analyzed for total protein quantification. The protein content determination was carried out with the Bradford test according the following protocol: 1) 250 μL of Brilliant Blue were added to a plate; 2) samples were tested diluted 1:10 and were out of the calibration range therefore were diluted 1:20 in saline and retested. 3) five μL of saline solution (blank), 5 μL of samples were added to the plate. Calibration was done in triplicate as well as samples; 4) samples were shaken for 30 sec; 5) plate was incubated for 10 min a R.T.; 6) plate was read at 595 nm.

ii. Results

1. Well-Being and Body Weight

All mice underwent the protocol of exercise/treatment without showing any sign of stress (lack of appetite, abnormal body weight loss, hair loss, stereotypic or aggressive behavior, etc.) or macroscopic alterations of vital functions. No significant variations in the body weight of animals, either treated or not, were observed throughout the experimental window.

2. Forelimb Grip Strength

The values of maximal forelimb force normalized to body weight measured at each weekly timepoint are shown in FIG. 1.

At T0, the values of the different experimental groups were substantially overlapping.

From T1 to T4, all mice treated with BCAA, BCAA and L-Alanine and BCAA and L-Alanyl-L-alanine showed higher force values with respect to vehicle-treated nice.

The addition of L-Alanine or L-Alanyl-L-alanine to BCAAs results in a stronger forelimb.

At T3 and T4, mice treated with BCAA and L-Alanyl-L-alanine were significantly stronger with respect to mice treated with BCAA and L-alanine (FIG. 1).

These data show that the supplementation with L-Alanyl-L-alanine improves muscle function and force after the treatment: this demonstrate that the formulation is effective in protecting against muscle weakness both in physiological and pathological conditions, 3. Determination of the Protein Content of Muscles Gastrocnemius muscle homogenates analyzed with the Bradford assay indicated a significant increase of total protein content in all treated groups compared to vehicle (125±13 mg/g tissue). In particular, group BCAA and L-Alanyl-L-alanine (192±8 mg/g tissue) showed the higher protein contents compared to BCAA and L-alanine (162±18 mg/g tissue) and BCAA group (142±10 mg/g tissue).

Figure 2:
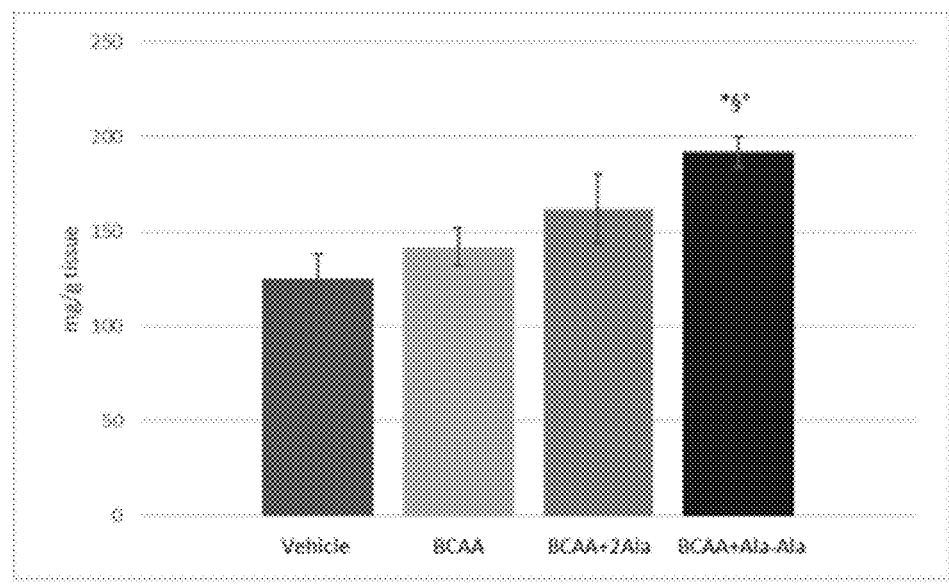
FIG. 2 shows the protein content measured by Bradford assay in homogenates of Gastrocnemius muscle of mice treated with Vehicle, BCAA (BCAA), BCAA plus L-Alanine (BCAA+2Ala) or BCAA plus L-Alanyl-L-alanine (BCAA+Ala-Ala), as described in Example 1 (BCAA+Ala-Ala * vs Vehicle $p<0.005$; § vs BCAA $p<0.01$; ° vs BCAA+2Ala $p<0.05$).

Data are reported in FIG. 2 as mean±S.E.M.

These data show that the supplementation with L-Alanyl-L-alanine increases the muscle protein content: this can led to the preservation of muscle weight, which may result advantageous to the affected skeletal muscle for functional recovery.

4. Salivary IgA Levels

Figure 3:
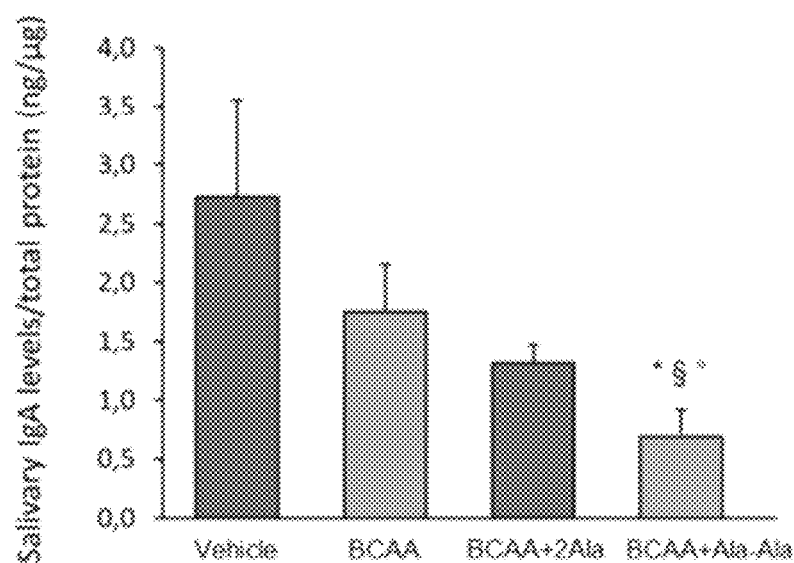
FIG. 3 shows salivary IgA levels normalized to total protein (ng/μg) in mice treated with Vehicle, BCAA (BCAA), BCAA plus L-Alanine (BCAA+2Ala) or BCAA plus L-Alanyl-L-alanine (BCAA+Aa-Ala), as described in Example 1 (* BCAA+Ala-Ala vs Vehicle $p<0.005$; § vs BCAA $p<0.01$; ° vs BCAA+2Ala $p<0.01$).

IgAs are markers that indicate the level of inflammation of the upper respiratory tract. The levels of IgA in saliva samples, collected right before sacrifice of each mouse, are shown normalized to total protein values (ng/µg) in FIG. 3. Salivary IgA levels of mice treated with BCAA, BCAA and L-alanine and BCAA and L-Alanyl-L-alanine were significantly reduced with respect to vehicle-treated ones. IgA levels of mice treated with BCAA and L-Alanyl-L-alanine and were significantly lower compared to any of the other groups.

These data show that supplementation with BCAA and L-Alanyl-L-alanine has an improved efficacy compared to BCAA and L-alanine in protecting muscle from wasting in pathological conditions and in preventing the onset of overtraining.

5. Plasma Level of Lactate Dehydrogenase (LDH)

Figure 4:
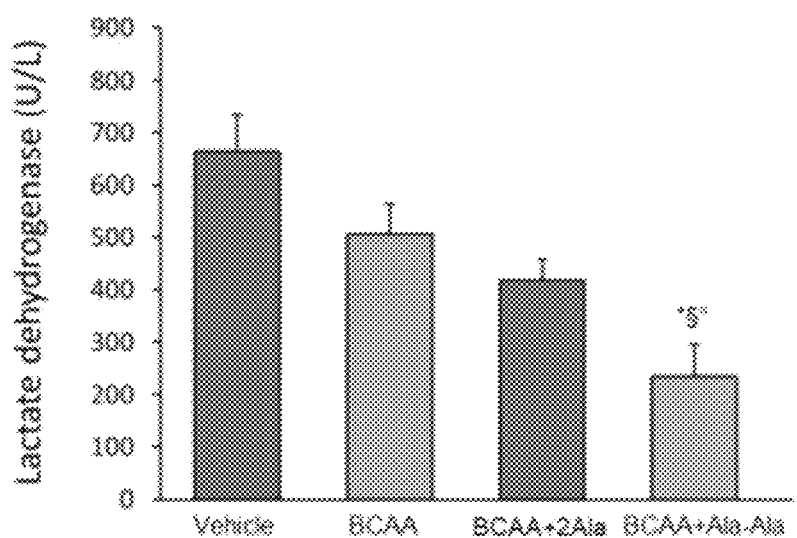
FIG. 4 shows plasma lactate dehydrogenase levels (U/L) in mice treated with Vehicle, BCAA (BCAA), BCAA plus L-Alanine in a weight ratio 1:2 (BCAA+2Ala) or BCAA plus L-Alanyl-L-alanine (BCAA+Ala-Ala), as described in Example 1. (* BCAA+Ala-Ala vs Vehicle $p<0.005$; § vs BCAA $p<0.01$; ° vs BCAA+2Ala $p<0.01$).

Plasma concentration of LDH enzymes assessed in plasma samples of mice is shown in FIG. 4. All three treatment showed a clear and significant trend toward the reduction of LDH plasma levels with respect to vehicle. LDH levels of mice treated with BCAA and L-Alanyl-L-alanine and were significantly lower compared to any of the other groups.

These data show that supplementation with BCAA and L-Alanyl-L-alanine has an improved efficacy compared to BCAA and L-alanine in protecting the structural integrity and metabolism of skeletal muscle during long-lasting exercise.

Example 2—Pharmacokinetic Study

The aim of the study was to compare the exposure of L-Leucine-13C6, 15N, L-Isoleucine-13C6, 15N, L-Valine-13C5, 15N in plasma after their administration alone or in association with L-Alanine or L-Alanyl-L-alanine in the mouse. Plasma samples were analyzed by dean-up and derivatization using the EZfaast™ amino acid analysis kit (Phenomenex) and analyzed by UPLC-MSMS.

i. Methods

Animals and Maintenance

CD1 mouse with body weights of 25-30 gr at the time of the treatment were used in this study, approximate age was about 4 weeks according to growth curve. The animals were originally supplied by Harlan, Italy. Once receipt from the supplier, the animals were subjected to health examinations and acceptance. The animals were housed, in a group of five, in cages suitable for the species. The animals were acclimatized to local housing conditions for approximately 5 days. The animals were routinely kept in the following environment except for short periods of time where experimental procedures dictated otherwise. The animals were housed in a single, exclusive room, air conditioned to provide a minimum of 15 air changes/hour. The environmental controls were set to maintain temperature within the range 22° C. and relative humidity within the range 50 to 60% with an approximate 12 hour light and 12 hour dark cycle that is controlled automatically. Food (Mucedola Standard GLP diet) and water were available ad libitum throughout the study. All animals were weighed on the day of each treatment and assigned randomly into groups uniquely identified with a coloured spray on the back before the experiment. Clinical signs were monitored at regular intervals throughout the study in order to assess any reaction to treatment. The experiment was carried on in agreement with the Italian Law (D. L.vo 26/2014). Blood samples (50-60 µL) were collected in heparinized eppendorfs (Heparin Vister 5000 U.I/mL), gently mixed and placed immediately on ice; then eppendorfs were centrifuged (3500×g, at 4° C. for 15 min) and the resulted plasma collected and transferred to uniquely labelled eppendorfs and frozen at −80° C. till the analysis. At the end of the study animals were sacrificed by exsanguination under deep isoflurane anaesthesia.

Groups and Doses

Fasted animals were divided in 4 groups of 6 mice each and the different groups were subjected to the following treatments. The administrated volume was 15 mL/kg, whereas the vehicle used for the study was a 1.5% w/w citric acid aqueous solution.

1) Group BCAA:
L-Leucine-13C6,15N 328 mg/kg; L-Isoleucine-13C6,15N 164 mg/kg; L-Valine-13C5,15N 164 mg/kg.

2) Group BCAA+Ala:
L-Leucine-13C6,15N 328 mg/kg; L-Isoleucine-13C6,15N 164 mg/kg; L-Valine-13C5,15N 164 mg/kg and L-Alanine 328 mg/kg.

3) Group BCAA+Ala-Ala
L-Leucine-13C6,15N 328 mg/kg; L-Isoleucine-13C6,15N 164 mg/kg; L-Valine-13C5,15N 164 mg/kg plus L-Alanine 328 mg/kg.

Bleeding Schedule and Feeding Regimen

Animals were fasted form the night before the administration and food was re-inserted in the cages 3 hours after the administration. Serial sampling at 15 min, 30 min, 1 h, 3 h, 8 h, 24 h was carried out collecting about 50-60 µL of blood at each time point.

ii. Results

Figure 5A:
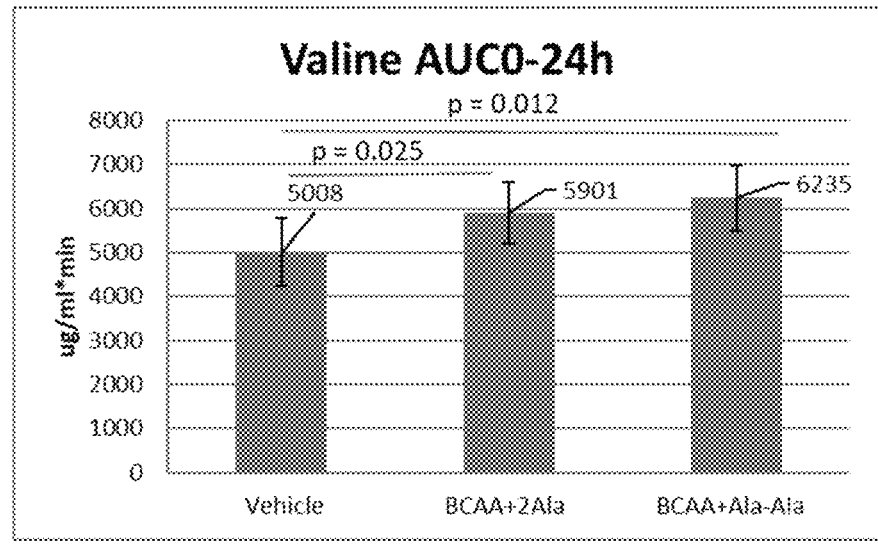
FIG. 5 shows the area under the curve from 0 to 24 hours (AUC0-24 h, μg/ml*min) of Valine (panel A), Leucine (panel B) and Isoleucine (panel C), measured after administration to mice of BCAA alone (BCAA), BCAA plus L-Alanine (BCAA+2Ala) or BCAA plus L-Alanyl-L-alanine (BCAA+Ala-Ala), as described in Example 2.
Figure 5B:
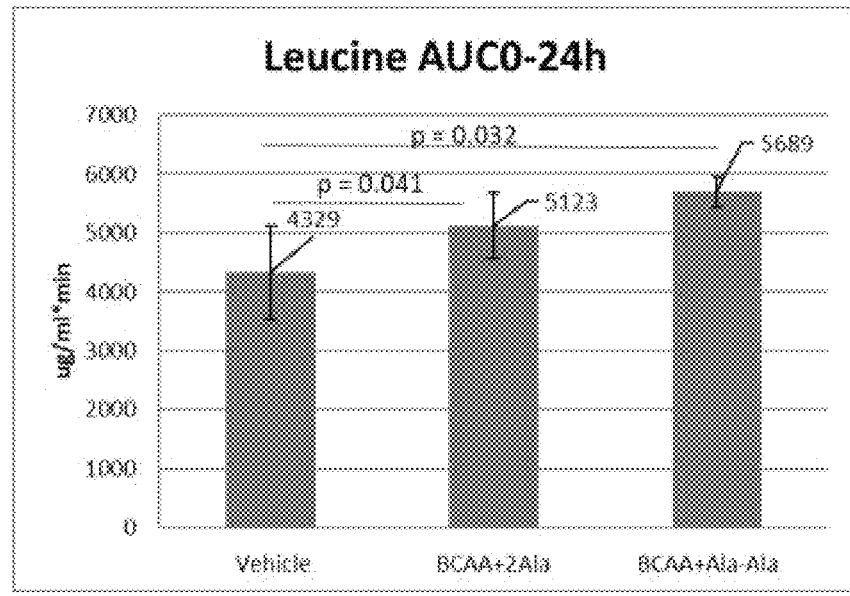
Figure 5C:
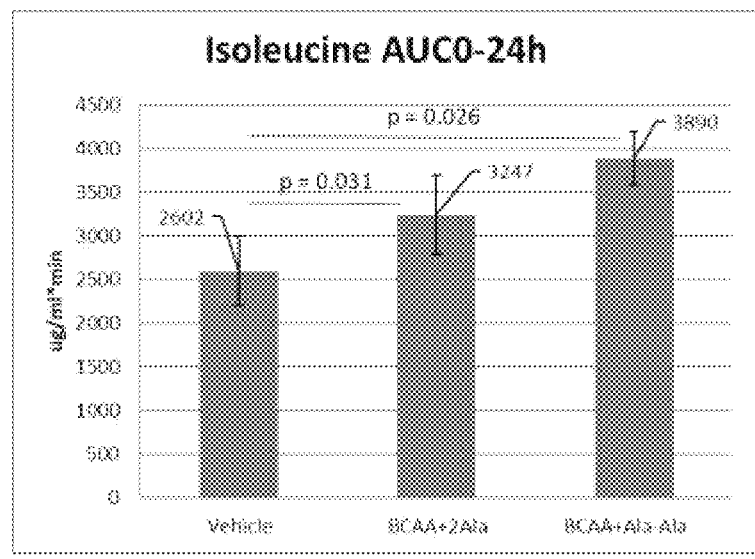
Figure 6A:
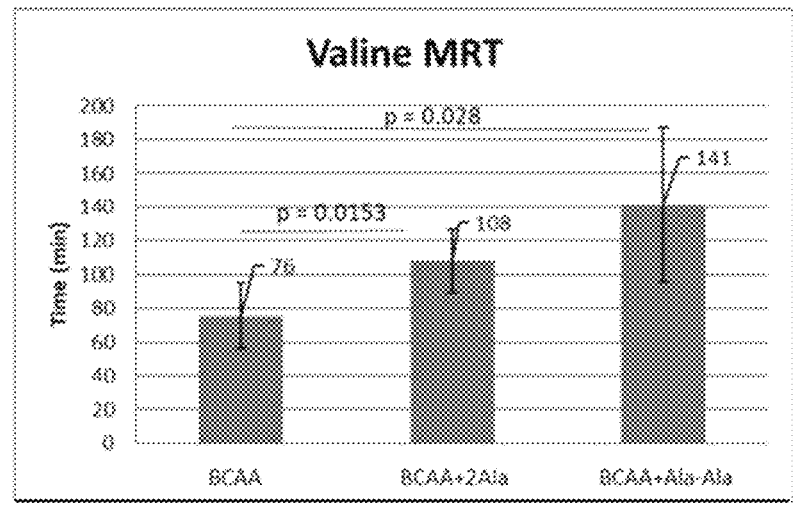
FIG. 6 shows the mean±SD of mean residence time (MRT) of Valine (panel A), Leucine (panel B) and Isoleucine (panel C), measured after administration to mice of BCAA alone (BCAA), BCAA plus L-Alanine (BCAA+2Ala) or BCAA plus L-Alanyl-L-alanine (BCAA+Ala-Ala), as described in Example 2.
Figure 6B:
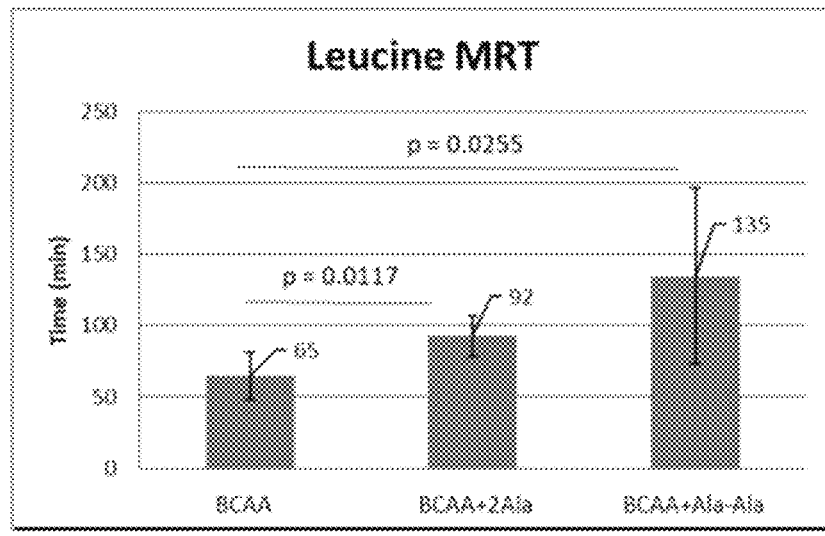
Figure 6C:
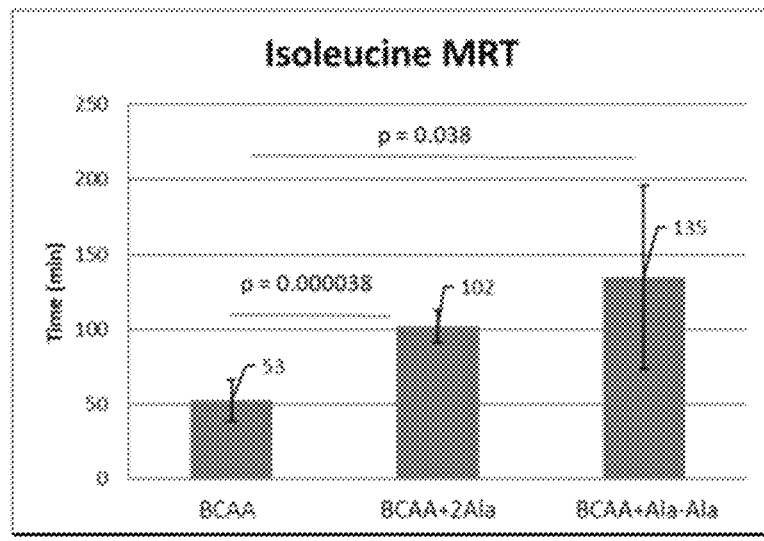

AUCs±SD for each single labeled amino acids were calculated for the time intervals 0-24 hrs and are reported in the FIGS. 5A, B and C. The mean±SD of mean residence time (MRT) for each labelled amino acids are reported in FIGS. 6A, B and C.

Plasma concentrations of the labelled amino acids were significantly increased with the administration of Alanine and L-Alanyl-L-alanine with the latter showed the highest concentrations (FIGS. 5A, B, C). Mean resident time values were significantly increased compared to BCAA groups, with the mice treated with BCAA plus L-Alanyl-L-alanine that showed the highest values. There were no differences in the other calculated pharmacokinetic parameters (Cmax, Tmax and T1/2) among the three groups.

Example 3—Oral Glucose Tolerance Test in the Mice

Oral glucose tolerance test (OGTT) was evaluated in mice pretreated with an oral administration of 15 mL/kg of vehicle (1.5% w/w citric acid aqueous solution), or of the composition BCAA plus L-alanine or BCAA plus L-Alanyl-L-alanine at the doses described in Example 1 and dissolved in 1.5% w/w citric acid aqueous solution. The administration volume of each solution was 15 m/kg. Mice were starved overnight, weighted and each one of the above treatments was orally administrated as described above.

Forty-five minutes following the oral administration of the pretreatment, a bolus of 20% glucose (2 mg/g body weight) was orally given to the mice and blood glycaemia was measured at time −45', 0', 15'. 30', 60', 90' and 120' by tail vein bleeding with a portable glucometer (Johnson & Johnson).

Figure 7:
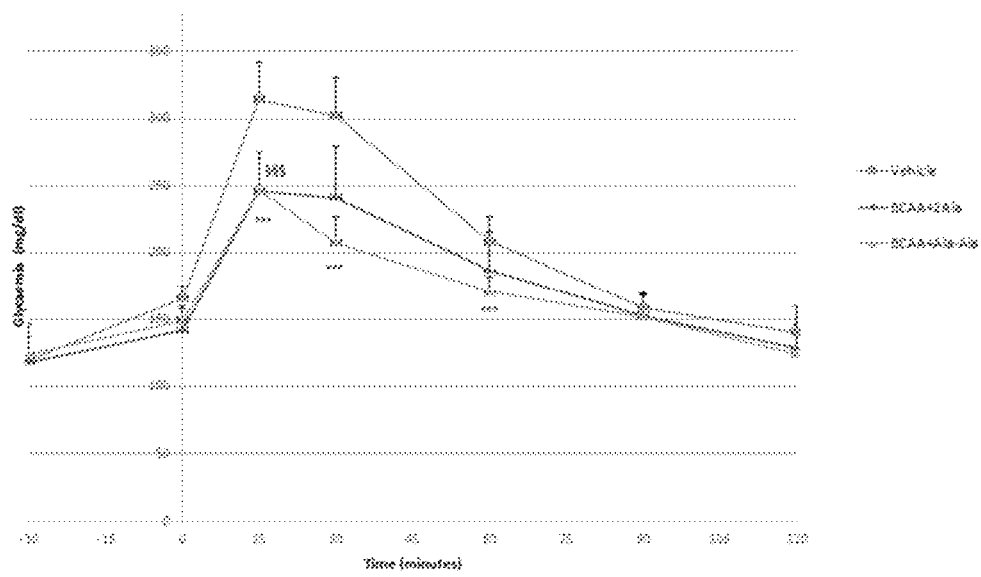
FIG. 7 shows the glycemic curve after administration of a bolus of glucose in mice pretreated with Vehicle, BCAA plus L-Alanine (BCAA+2Ala) or BCAA plus L-Alanyl-L-alanine (BCAA+Ala-Ala), as described in Example 3 (BCAA+Ala-Ala vs Vehicle *** $p<0.005$; BCAA+2Ala vs Vehicle §§§ $p<0.005$).

FIG. 7 shows the glycemic curves obtained in mice with each of the pre-treatments. Following glucose bolus administration, BCAA plus L-Alanyl-L-alanine treated mice showed significantly lower glycemic levels at 15, 30 and 60 minutes, whereas BCAA plus L-Alanine only showed a significant decrease of glycemic levels at 15 minutes.

The data obtained demonstrated the stronger ability (i.e. its efficacy at more time-points) of L-Alanyl-L-alanine with respect to L-Alanine to improve glucose tolerance in mice.

Figure 8:
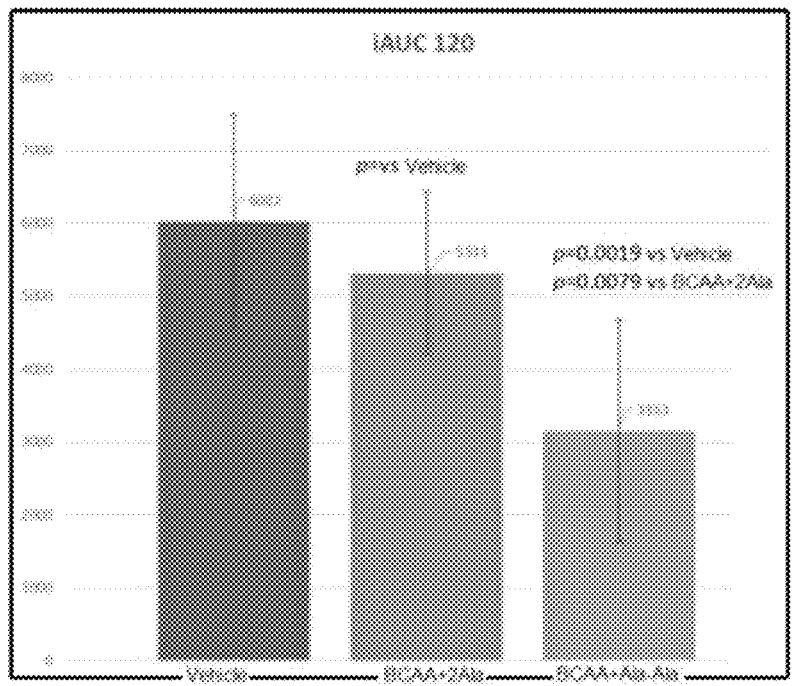
FIG. 8 shows the incremental area under the curve (iAUC) of glycemia measured in the 120 minutes after administration of a bolus of glucose in mice pretreated with Vehicle, BCAA plus L-Alanine (BCAA+2Ala) or BCAA plus L-Alanyl-L-alanine (BCAA+Ala-Ala), as described in Example 3.

The incremental area under the curve for blood glucose excursion was then calculated from t=0 to t=120 minutes (iAUC0-120) and showed in FIG. 8.

As can be seen from the figure, BCAA plus L-Alanyl-L-alanine administration effected in a significant manner glucose tolerance compared to vehicle and BCAA plus L-alanine treated mice.

These data show that the oral administration of BCAA plus L-Alanyl-L-alanine induced the amelioration of glucose tolerance in healthy C57BL/6 mice. This is in accordance with the data obtained in the pharmacokinetic study, showing that L-Alanyl-L-alanine increases the exposition of BCAA compared to L-Alanine. Therefore, this rising in plasma BCAA led to an increase in insulin secretion ater the glucose bolus, with the consequence decrease of plasma glucose content. In conclusion, we demonstrated the greater plasma glucose-lowering action of the dipeptide L-Alanyl-L-alanine compared to L-Alanine.

Example 4—Preclinical Evaluation of the Efficacy on Improving Muscle Function in a Mouse Model of Muscular Atrophy (HU Mouse)

i. Methods

Experiments were performed in accordance with the Italian Guidelines for the use of laboratory animals (Italian legislative decree 2014 n.26), which conforms with the European Union Directive for the protection of experimental animals (2011/63/EU), and received approval from the Italian Ministero della Salute (D.M. n.133/2000-B).

Adult male C57BL/6J mice (12-14 weeks-old) were purchased from Charles River (Calco, Italy). Mice were subdivided in 4 groups of 8 animals, one control group and 3 hindlimb-unloaded (HU) groups. In details:

Control Group:

the mice were housed individually in control conditions for 4 weeks.

Hindlimb-Unloaded (HU) Groups:

A muscle unloading protocol was used, similar to that used previously for HU rats (Pierno S, et al. J Physiol 2007; 584:983-95). In details, the animals were suspended individually in special cages for 2 weeks. A thin string was linked at one extremity to the tail by sticking plaster and at the other extremity to the top of the cage. The length of the string was adjusted to allow the animals moving freely on the forelimbs, while the body was inclined at 30-40° from the horizontal plane. All mice had water ad libitum and received 8 g a day of standard rodent chow. The food remaining on the day after was weighted to calculate daily food consumption.

The different HU groups were treated as follows:
Vehicle: the mice were housed individually for 4 weeks, and were hindlimb unloaded for the last 2 weeks.
During this period, they received the vehicle (water).
BCAA: the mice were housed individually for 4 weeks, received BCAA (L-Leucine 328 mg/kg; L-Isoleucine 164 mg/kg; L-Valine 164 mg/kg) once a day for 4 weeks, and were hindlimb unloaded for the last 2-weeks.
BCAA+Ala-Ala: the mice were housed individually for 4 weeks, received mix BCAA plus L-Alanyl-L-alanine (L-Leucine 328 mg/kg; L-Isoleucine 164 mg/kg; L-Valine 164 mg/kg plus L-Alanyl-L-alanine 328 mg/kg) once a day for 4 weeks, and were hindlimb unloaded for the last 2-weeks.

Each formulation was prepared dissolving the powder in filtered tap water, in order to obtain the final concentration. This was obtained by direct preparation, considering the weekly amount of water consumed by each mouse and its body weight. The duration of the treatment was of 4 weeks.

The HU animals were examined daily over the entire HU period for behavior, cleanliness, aspect of hairs and eyes, food and water consumption. Daily food intake was measured as the mean value of the quantity of commercial food (in grams) eaten each day over 14 days by the mice belonging to CTRL and HU groups.

The mice were given a standard amount of food (10 g) each morning, and the remaining food was weighted on the morning of the following day. We obtained the daily intake by subtraction, and a mean daily intake over 14 days was calculated for each animal. The final result reports the mean±SEM from n animals in each experimental group. At the end of the treatment period, mice were weighted and deeply anesthetized with intraperitoneal injection of urethane (1.2 g/kg body weight) to allow removing of hind limb skeletal muscles, which are the soleus (Sol), Extensor Digitorum Longus (EDL), and gastrocnemius (Gas). These muscles were used immediately for electrophysiological and functional studies or frozen in liquid nitrogen and stored at −80° C. for further biochemical and gene expression analysis. After surgery, animals were euthanized by an overdose of urethane. All efforts were made to minimize animal suffering.

In Vivo Torque Protocol

In vivo maximal isometric torque of the plantar flexor muscle group (GC and soleus muscles) was assessed at the various time points of chronic exercise or cage-based activity. Mice were anesthetized via inhalation (~4% isoflurane and 1.5% $O_2$ l/min) and placed on a thermostatically controlled table; anesthesia was maintained via a nose cone (~2% isoflurane and 1.5% $O_2$ l/min). The right hindlimb was shaved and aseptically prepared, and the foot was placed on the pedal connected to a servomotor (model 300C-LR; Aurora Scientific, Aurora, ON, Canada). Contractions were elicited by percutaneous electrical stimulation of the tibial nerve via needle electrodes (Chalgren Enterprises) connected to a stimulator (model 701B; Aurora Scientific) to induce contraction of the group of plantar flexor muscles. The current was adjusted from 30 to 50 mA until maximal isometric torque was achieved. A series of stimulations were then performed at increasing frequencies: 1, 10, 30, 50, 80 and 100 Hz with a pulse train of 200 ms. Data were analyzed using Dynamic Muscle Analysis software (DMAv5.201;

Aurora Scientific) to obtain torque, which was normalized to mouse body mass. Normalized values were used to construct torque-frequency curves.

ii. Results

Well-Being and Body Weight

All mice underwent the protocol of exercise/treatment without showing any sign of stress (lack of appetite, abnormal body weight loss, hair loss, stereotypic or aggressive behavior, etc.) or macroscopic alterations of vital functions. No significant variations in the body weight of animals, either treated or not, were observed throughout the experimental window.

In Vivo Torque

Figure 9:
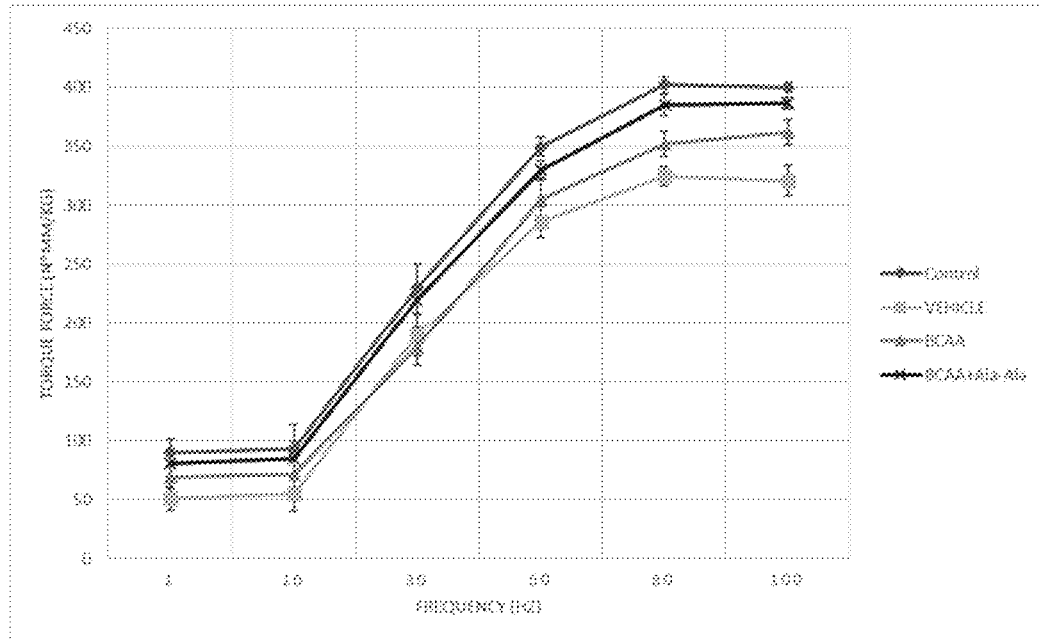
FIG. 9 shows the force-frequency curves (N*mm/kg) produced by torque of the plantar flexor muscles of control mice and of mice subjected to hindlimb-unloading and treated with Vehicle, BCAA or BCAA plus L-Alanyl-L-alanine (BCAA+Ala-Ala), as described in Example 4.

In vivo neuromuscular function was assessed by measuring the torque produced by hind limb plantar flexor muscles in anesthetized mice, independently from animal willingness. As shown in FIG. 9, mice treated with BCAA plus L-Alanyl-L-alanine resulted to have the significantly highest torque frequency curve among the treated groups. In particular, we found that the maximal torque value, produced at 100 Hz, almost overlapped that from the sedentary mice group (398±7 vs 379±8 N*mm/kg; n=8).

The torque measurements in anesthetized animals confirmed the muscle disuse condition (i.e. weakness) in hindlimb-unload mice compared to the control group.

Furthermore, the data clearly show that the treatment with BCAA plus L-Alanyl-L-alanine improves the neuromuscular function of the plantar flexor muscle (mainly GC and soleus muscles) with respect to vehicle and BCAA, and with values of torque force close to those observed for the control group.

The invention claimed is:

1. A composition comprising branched-chain amino acids (BCCAs) L-Leucine, L-Valine and L-Isoleucine in combination with peptide L-Alanyl-L-alanine.

2. The composition according to claim 1, wherein the weight ratio L-Leucine: L-Valine: L-Isoleucine is between 2:1:1 and 8:1:1.

3. The composition according to claim 2, wherein the weight ratio L-Leucine: L-Valine: L-Isoleucine is 2:1:1 or 4:1:1 or 8:1:1.

4. The composition according to claim 1, wherein the weight ratio L-Leucine: L-Valine: L-Isoleucine: L-Alanyl-L-alanine is between 2:1:1:1 to 2:1:1:3.6.

5. The composition according to claim 4, wherein the weight ratio L-Leucine: L-Valine: L-Isoleucine: L-Alanyl-L-alanine is 2:1:1:2.5 or 2:1:1:2.

6. The composition according to claim 1, which is a dietary supplement.

7. The composition according to claim 1, which is a pharmaceutical composition.

8. The composition according to claim 1, which is packaged for oral administration.

9. The composition according to claim 1, containing the following amounts of BCAAs and dipeptide per unit dose: between 0.6 and 1 g of L-Leucine, between 0.3 and 0.5 g of L-Isoleucine, between 0.3 and 0.5 g of L-Valine and from 0.5 g to 1.5 g of L-Alanyl-L-alanine.

10. The composition according to claim 9, containing the following amounts of BCAAs and dipeptide per unit dose: 0.8 g of L-Leucine, 0.4 g of L-Isoleucine, 0.4 g of L-Valine and 0.8 g of L-Alanyl-L-alanine.

11. A method of preventing, ameliorating and/or treating muscle wasting associated with:
   i. pathological conditions;
   ii. age-related conditions; or
   iii. malnutrition, immobility or fasting,
in a subject in need thereof, comprising administration of the composition according to claim 1.

12. The method according to claim 11, wherein the pathological condition is selected from the group consisting of neuromuscular degenerative disorders; chronic obstructive pulmonary disorder; cancer-associated cachexia; diabetes; renal failure; cardiac failure; Cushing syndrome; sepsis; burn injuries; uremia; cirrhosis; and AIDS.

13. The method according to claim 11, wherein the age-related condition is sarcopenia.

14. A method of improving muscular performance and/or recovery, and/or to reducing muscular fatigue before, after or during physical exercise in a subject in need thereof, comprising administration of an effective amount of the composition according to claim 1.

15. The method according to claim 12, wherein the neuromuscular degenerative disorder is muscular dystrophy or muscular atrophy.

* * * * *